United States Patent [19]

Wong

[11] Patent Number: 4,529,598
[45] Date of Patent: Jul. 16, 1985

[54] INSECT REPELLENT COMPOUNDS

[75] Inventor: Rayman Y. Wong, Richmond, Calif.

[73] Assignee: Stauffer Chemical Company, Westport, Conn.

[21] Appl. No.: 74,038

[22] Filed: Sep. 10, 1979

Related U.S. Application Data

[63] Continuation-in-part of Ser. No. 69,523, Aug. 24, 1979, abandoned, which is a continuation of Ser. No. 910,817, May 30, 1978, abandoned.

[51] Int. Cl.³ .................. A01N 43/40; A61K 7/42; A61K 9/12
[52] U.S. Cl. .................. 514/277; 424/DIG. 13; 424/47; 424/59; 424/60
[58] Field of Search .................. 424/263; 546/341

[56] References Cited

U.S. PATENT DOCUMENTS 2,138,031 11/1938 Graves .................. 260/2
2,138,763 4/1938 Graves .................. 260/83
2,554,947 5/1951 Joos .................. 260/486
3,290,211 12/1966 Schickedantz .................. 424/DIG. 10
3,438,993 4/1969 Wilbert et al. .................. 260/295
3,586,711 6/1971 Korshunov et al. .................. 544/171
4,093,622 6/1978 Henrick et al. .................. 260/295 R

FOREIGN PATENT DOCUMENTS 2157684 6/1973 France .................. 424/263

Primary Examiner—Dale R. Ore
Attorney, Agent, or Firm—Joel G. Ackerman

[57] ABSTRACT

Compounds having the formula

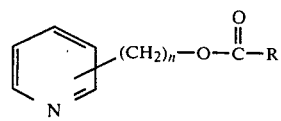

in which R is $C_2$–$C_5$ alkyl or $C_3$–$C_5$ alkenyl and n is an integer from 1 to 3, are effective to repel insects.

8 Claims, No Drawings

INSECT REPELLENT COMPOUNDS

CROSS-REFERENCE TO RELATED APPLICATIONS

This is a continuation-in-part of application Ser. No. 69,523, filed Aug. 24, 1979, now abandoned which is a continuation of application Ser. No. 910,817, filed May 30, 1978, now abandoned.

BACKGROUND OF THE INVENTION

This invention relates to novel compounds having the formula

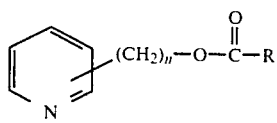

in which R is $C_3-C_5$ alkyl or $C_3-C_5$ alkenyl and n is an integer from 1 to 3. The terms "alkyl" and "alkenyl" include both straight and branched chain groups. In a preferred embodiment, n is 3 and R is 2-methyl-1-propenyl, $-CH=C(CH_3)_2$. A preferred compound of this type is gamma-(3-pyridyl)-propyl-3-methyl-2-butenoate (n=3, R=2-methyl-1-propenyl, and the ester moiety is substituted at the 3-position on the pyridyl ring). Other compounds include the 2-pyridyl and 4-pyridyl isomers of this preferred compound, the methyl analog (n=1, R=2-methyl-1-propenyl, substitution at the 3-position on the ring) and gamma-(3-pyridyl)-propyl isovalerate (n=3, R=isobutyl, substitution at the 3-position on the ring).

The compounds of this type can be prepared by reaction of an appropriate pyridyl alkanol with an acyl chloride:

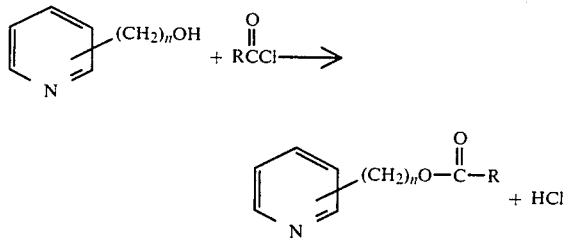

The reaction is generally conducted at temperatures of about 5°–15° C., in the presence of a solvent such as methylene chloride, chloroform, other chloro-carbon solvents or ethers, and a hydrogen chloride acceptor. For preparation of compounds in which R is alkyl, suitable hydrogen chloride acceptors include pyridine, triethylamine and sodium hydroxide. For compounds in which R is alkenyl, pyridine is used. The product is recovered by conventional extraction, washing and filtration steps.

Preparation of such compounds is illustrated by the following example.

EXAMPLE 1

Preparation of Gamma-(3-Pyridyl)-Propyl-3-Methyl-2-Butenoate

Into a flask was introduced a solution of 5.00 grams (0.036 mole) of 3-(3-pyridyl)-1-propanol and 3.16 grams (0.040 mole) pyridine (reagent grade) in 50 milliliters of methylene chloride (reagent grade). A clear brown solution was formed which was then cooled to 0° C. with an ice-water bath. There was then added 4.74 grams (0.040 mole) of 3,3-dimethylacryloyl chloride (97% pure), dropwise, over a period of 10 minutes, the temperature being maintained between 5° and 15° C. The solution became deep red. Following the addition, the solution was stirred at 0° C. for one hour; the cooling bath was removed and the solution stirred at room temperature for three additional hours.

The solution was then diluted with 50 milliliters of methylene chloride and poured into 50 milliliters of water; the organic layer was separated and washed with 10 milliliters of a saturated sodium bicarbonate solution and three portions each of 10 milliliters of water until the pH of the solution was measured at 7, followed by washing with 10 milliliters of sodium chloride and drying over sodium sulfate. The dried organic solution was filtered through sodium sulfate and the solvent was removed under vacuum to yield 8.08 grams (101.3% of theoretical) of the desired compound, a crude clear orange oil, $n_D^{30}$ 1.5153. The structure of the compound was confirmed by infrared and nuclear magnetic resonance spectra.

Insect Repellent Test

The compound prepared according to Example 1 was tested for insect repellency by the following procedures:

Mosquito Repellent Evaluation:

A paper cup filled with pupae of the mosquito *Culex pipiens quinquefasciatus* (Say) was placed in a screen cage and the pupae allowed to emerge into adults. Sugar cubes were then saturated with 0.8 milliliters of acetone containing the test compound and, for a control, with the same amount of acetone alone. Concentrations of the test compound were utilized beginning at 1% and proceeding to lower concentrations. After the cubes dried, they were put into the screen cage. Repellency was determined by the number of mosquito adults lighting and feeding on the sugar cubes, with observations being made daily. New adult mosquitos were periodically added to the cages until all sugar cubes became non-repellent. The number of days of complete repellency of mosquitos from the sugar cubes were recorded. Comparative tests were similarly conducted using the compound N,N-diethyl-m-toluamide, commercially manufactured and employed as an insect repellent, and generally known by the generic name "deet". The results of the tests of deet and the compound of Example 1 are shown in the following Table I, the numbers of each column representing the number of days of complete repellency observed using the specified concentration.

TABLE I

| | CONCENTRATION, % | | | | |
|---|---|---|---|---|---|
| | 1 | 0.5 | 0.3 | 0.1 | 0 (acetone only) |
| Example 1 | >60 | 27 | 26 | 5 | 0 |
| deet | 11–13 | 6.7 | 5 | 5 | 0 |

Thus, at a concentration as low as 0.1%, the new compound was as effective as deet in repelling mosquitos. At higher concentrations, it was more effective than deet. At a concentration of 1% of the new compound in the solution, after 60 days the mosquitos were still repelled from the sugar cube and the tests were terminated.

Houseflies:

The insect utilized for this test was housefly, *Musca domestica* (L.) One hundred (100) houseflies of mixed sexes were placed in test cages. Each test cage consisted of a 16 ounce cup, covered with tulle netting, and having two ¾ ounce cups stapled on opposite sides of the upper, interior perimeter. One of the small cups contained a sugar cube saturated with 0.8 milliliters of acetone containing a specific concentration of the test compound. The cube was dried and weighed before being placed in the cup. The other small cup contained a water-saturated cotton plug. The test cages were placed on a turntable and rotated at 1.5 revolutions per minute to keep the flies randomly distributed inside the cages. After 72 hours the flies in each cage were anesthetized with carbon dioxide. The sugar cubes were removed and reweighed and the percentage weight loss (due to consumption by the flies) recorded. The cubes with the least weight loss are considered to show the greatest repellency. Test concentrations of the compound ranged from 1% down to 0.1%. The weight losses of the sugar in percent, is shown in the following Table II.

TABLE II

| | CONCENTRATION. % | | | | |
|---|---|---|---|---|---|
| | 1 | 0.5 | 0.3 | 0.1 | 0 (Acetone only) |
| Example 1 | 4.45 | 5.91 | 6.73 | 9.5 | 12.7 |
| deet | 7.09 | 7.12 | 9.69 | 11.0 | 12.7 |

The novel compounds of this invention may be used as insect repellents in diluted or undiluted form. When used in a diluted form, the compounds may be embodied into compositions containing a relatively high or relatively low concentration of the active compound. For example, the active compound can be incorporated into relatively high concentration compositions such as wet sprays or solutions in alcohol or other suitable solvents. Such compositions may contain, in addition to the active compound, adjuvants, such as emulsifying agents, surface active agents, antioxidants, and propellants, which may be found normally in insect repellant preparations. The active compounds of this invention may be employed as the sole active component of such compositions or can be used in admixture with other compounds having similar or different utility. For example, the novel compounds may be incorporated into creams, lotions, powders, suntan oils, insecticides and other preparations, which may contain pesticidal or other useful substances, as well as to compositions of various types used for treating fabrics or articles of clothing to render them insect repellent. In general, compositions for repellent use may contain from 0.5 as high as 80 weight %, preferably from 2 to about 40 weight %, of the novel compound.

What is claimed is:

1. A compound having the formula

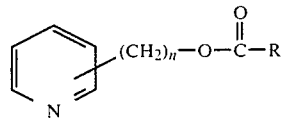

in which R is $C_3$–$C_5$ alkyl or $C_3$–$C_5$ alkenyl and n is 3.

2. A compound according to claim 1 which R is 2-methyl-1-propenyl, and the ester moiety is substituted at the 3-position on the pyridine ring.

3. An insect repellent composition containing an amount of a compound having the formula

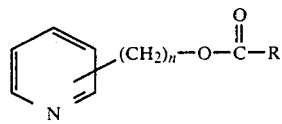

in which R is $C_3$–$C_5$ alkyl or $C_3$–$C_5$ alkenyl and n is 3, effective to repel insects, and an inert diluent or carrier.

4. A composition according to claim 3 containing an amount of a compound effective to repel mosquitos.

5. A composition according to claim 3 in which R is 2-methyl-1-propenyl, and the ester moiety is substituted at the 3-position on the pyridine ring.

6. A method of repelling insects from a locus to be protected therefrom, comprising applying to said locus an effective insect repelling amount of a compound having the formula

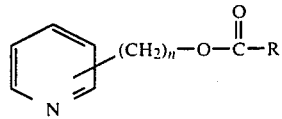

in which R is $C_3$–$C_5$ alkyl or $C_3$–$C_5$ alkenyl and n is 3.

7. A method according to claim 6 in which the compound is applied in an amount effective to repel mosquitos.

8. A method according to claim 6 in which R is 2-methyl-1-propenyl, and the ester moiety is substituted at the 3-position on the pyridine ring.

* * * * *